United States Patent [19]

Furusaki et al.

[11] 4,420,633

[45] Dec. 13, 1983

[54] PROCESS FOR THE PREPARATION OF AN ESTER OF FORMIC ACID

[75] Inventors: Shinichi Furusaki; Noriaki Manada; Hisao Yamashina; Masaoki Matsuda, all of Ube, Japan

[73] Assignee: Ube Industries, Ltd., Ube, Japan

[21] Appl. No.: 331,614

[22] Filed: Dec. 17, 1981

[30] Foreign Application Priority Data

Jan. 8, 1981 [JP] Japan ................................. 56-707

[51] Int. Cl.³ ........................ C07C 67/36; C07C 69/06
[52] U.S. Cl. .................................. 560/232; 560/204; 568/835; 568/909
[58] Field of Search ............................... 560/232, 265

[56] References Cited

U.S. PATENT DOCUMENTS 3,816,513  6/1974  Wakamatsu et al. ............... 560/232
3,994,960 11/1976  Yamazaki et al. ................. 560/232
4,229,589 10/1980  Nishimura et al. ................ 560/204
4,229,591 10/1980  Nishimura et al. ................ 560/204

*Primary Examiner*—Vivian Garner
*Attorney, Agent, or Firm*—Frishauf, Holtz, Goodman & Woodward

[57] ABSTRACT

There is disclosed a novel process for the preparation of an ester of formic acid which comprises subjecting hydrogen, carbon monoxide and an ester of nitrous acid to a catalytic vapor phase reaction in the presence of a platinum group metal or a salt thereof. The product obtained by the process according to the present invention does not substantially contain water and free formic acid. The ester of formic acid formed by the process according to the present invention can be separated and purified in a simple manner, e.g., by conventional distillation procedure.

20 Claims, No Drawings

PROCESS FOR THE PREPARATION OF AN ESTER OF FORMIC ACID

This invention relates to a process for preparing an ester of formic acid. More particularly, this invention relates to a process for preparing an ester of formic acid which comprises subjecting hydrogen, carbon monoxide and an ester of nitrous acid to a catalytic vapor phase reaction with each other in the presence of a platinum group metal or a salt thereof.

An ester of formic acid has widely been used for solvents, perfumeries, insecticides, fungicides, reagents for organic syntheses and so on.

An ester of formic acid has hitherto been prepared industrially by the so-called esterification reaction between formic acid and an alcohol in the presence of sulfuric acid. This conventional method has defects in that expensive formic acid must be used as a starting material and that the separation and purification of the desired product is difficult to achieve so that, when using conventional distillation, the obtained ester of formic acid is inevitably contaminated with the starting materials, i.e., formic acid and the alcohol.

In Japanese Provisional Patent Publication No. 138614/76, there has been proposed a process for preparing an ester of formic acid from an alcohol, carbon dioxide and hydrogen in the presence of a VIII group transition metal complex and a tertiary amine; and in Japanese Provisional Patent Publication No. 7612/78, there has been proposed a process for preparing an ester of formic acid from an alcohol, carbon dioxide and hydrogen in the presence of a VIII group transition metal complex and an alkali metal or an alkaline earth metal. However, these processes have disadvantages in that these processes rely upon a liquid phase reaction and a VIII group metal, which is difficult to be effectively recovered and reused, is employed as a catalyst; that it is necessary to add large amounts of an alkali metal, an alkaline earth metal and a basic substance such as a tertiary amine which must be separated after the reaction; that the yield of the desired product in terms of the amount of the catalyst is extremely low; and so on.

As a result of extensive studies to solve these problems, the present inventors have found that an ester of formic acid can be prepared, by a simple procedure, if hydrogen, carbon monoxide and an ester of nitrous acid are subjected to a catalytic vapor phase reaction with each other in the presence of a platinum group metal or a salt thereof, and accomplished the present invention.

The reaction of this invention is an entirely novel reaction which proceeds according to the following scheme.

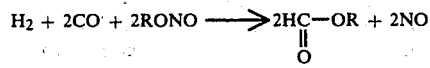

wherein R represents an alkyl group or cycloalkyl group.

In practicing the present invention, hydrogen, carbon monoxide and a gaseous ester of nitrous acid as such or after being diluted with an inert gas are subjected to reaction by introducing them in the vapor state onto a catalyst.

As the platinum group metal which is used as the catalyst in the present invention, there may be mentioned palladium, platinum, rhodium, ruthenium, iridium and the like. As the salt of the platinum group metal, there may effectively be used any salt which can be converted into a metal under the reaction conditions, for example, inorganic salts such as nitrates, sulfates, phosphates and halogenides and organic salt such as acetates, oxalates and benzoates. Further the complexes of these metal may be used for the purpose. Moreover, these platinum group metals or their salts may not necessarily be used alone, and they may be used in combination.

Preferably, these platinum group metals or their salts are used by being carried usually on a carrier such as activated carbon, alumina, silica, diatomaceous earth, pumice, zeolite, magnesium oxide, titanium oxide, molecular sieve, silicon carbide and the like. The amount of the platinum group metal carried on a carrier may preferably be in the range of 0.01–20% by weight, usually of 0.05–5% by weight.

The ester of nitrous acid which is preferably used in the process of this invention is an ester of nitrous acid with a saturated monohydric aliphatic alcohol having 1 to 8 carbon atoms or an alicyclic alcohol having 1 to 8 carbon atoms. As the alcohol component may be mentioned an aliphatic alcohol such as methanol, ethanol, n-propanol, isopropanol, n-butanol, isobutanol, sec-butanol, tert-butanol, n-amyl alcohol, isoamyl alcohol, hexanol, octanol, etc., and an alicyclic alcohol such as cyclohexanol, methylcyclohexanol, etc. These alcohol components may contain a substituent such as an alkoxy group which does not inhibit the reaction.

The ester of nitrous acid used in the present process need not necessarily be in a form of an ester of nitrous acid, and a compound which forms an ester of nitrous acid in the reaction system may also be used. It may also be advantageous to use an alcohol along with a nitrogen compound selected from the group consisting of nitrogen monoxide, nitrogen dioxide, dinitrogen trioxide and dinitrogen tetraoxide, and hydrates of these nitrogen compound instead of an ester of nitrous acid by introducing as occasion demands a gas containing molecular oxygen into the system. As the hydrates of these nitrogen oxides the following may effectively be used, nitric acid, nitrous acid and the like. An alcohol to be used in such cases is selected from the alcohols which are the constituents of the ester of nitrous acid as mentioned hereinbefore.

While the ratio of hydrogen, carbon monoxide and the ester of nitrous acid which are used in the present invention can be varied over a wide range, it is preferable to use hydrogen in an amount of 0.05 to 10 moles, particularly 0.07 to 5 moles relative to 1 mole of the ester of nitrous acid, and to use carbon monoxide in an amount of 0.1 to 100 moles, particularly 0.2 to 50 moles relative to 1 mole of the ester of nitrous acid.

While the reaction according to the present invention proceeds at a temperature of not less than 40° C. under a pressure of 0.1 to 100 atmospheres preferably at a temperature of 80° to 200° C. at ambient pressure up to around 20 atmospheres.

The process according to the present invention is practiced by using a reactor of fixed bed or fluidized bed. The contact time during which the gaseous material contacts with the solid catalyst is not more than 10 seconds, preferably 0.2 to 5 seconds.

In the product obtained by the process according to the present invention, water and free formic acid are not substantially included. The formed ester of formic acid can simply be separated and purified by conventional distillation.

Next, the present invention will be explained in more detail by way of Examples, which however should not be construed to limit the present invention. The tubular reactor used in Examples 1 to 18 is made of hard glass, having an inside diameter of 25 mm and a length of 200 mm.

EXAMPLE 1

In a tubular reactor, there was packed 10 ml. of a pellet catalyst (manufactured by Nippon Engerhard Co., Ltd.) in which 0.5% by weight of palladium was carried on alumina, followed by introduction of a gaseous mixture consisting of 26.7% by volume of carbon monoxide, 2.3% by volume of hydrogen, 7.2% by volume of methyl nitrite and 63.8% by volume of nitrogen at a rate of 42.6 l. per hour to subject the gaseous mixture to reaction at a reaction temperature of 120° C. under ambient pressure. According to a gas-chromatographic analysis of the reaction mixture, it was found that methyl formate was produced in a space time yield of 212 g./l.-catalyst.hr and small amounts of dimethyl oxalate and methanol were by-produced.

EXAMPLE 2

In a tubular reactor, there was packed 10 ml. of a 0.5 wt.% palladium-on-alumina catalyst (manufactured by Nippon Engerhard Co., Ltd.), followed by introduction of a gaseous mixture consisting of 30.5% by volume of carbon monoxide, 2.6% by volume of hydrogen, 1.8% by volume of n-butyl nitrite and 65.1% by volume of nitrogen at a rate of 37.4 l. per hour to subject the gaseous mixture to reaction at a reaction temperature of 120° C. under ambient pressure. According to a gas-chromatographic analysis of the reaction mixture, it was found that n-butyl formate was produced in a space time yield of 95 g./l.-catalyst.hr and small amounts of di-n-butyl oxalate and n-butanol were by-produced.

EXAMPLE 3

Experiment was run in the same manner as in Example 2 except that the composition of the gaseous starting materials was replaced by 27.9% by volume of carbon monoxide, 6.2% by volume of hydrogen, 1.7% by volume of n-butyl nitrite and 64.2% by volume of nitrogen. As the result, it was found that n-butyl formate was produced in a space time yield of 109 g./l.-catalyst.hr, and small amounts of di-n-butyl oxalate and n-butanol were by-produced.

EXAMPLE 4

Experiment was run in the same manner as in Example 2 except that the composition of the gaseous starting materials was replaced by 30.3% by volume of carbon monoxide, 2.6% by volume of hydrogen, 2.4% by volume of n-butyl nitrite and 65.5% by volume of nitrogen and that the catalyst was replaced by a 1.0 wt.% palladium-on-activated carbon catalyst. As the result, it was found that n-butyl formate was produced in a space time yield of 147 g./l.-catalyst.hr and small amounts of di-n-butyl oxalate and n-butanol were by-produced.

EXAMPLE 5

Experiment was run in the same manner as in Example 4 except that the catalyst was replaced by 1.0 wt.% palladium-on-silicon-carbide. As the result, it was found that n-butyl formate was produced in a space time yield of 202 g./l.-catalyst.hr and small amounts of di-n-butyl oxalate and n-butanol were by-produced.

EXAMPLES 6 TO 10

In a tubular reactor, there was packed 10 ml. of a 1.0 wt.% palladium-on-silicon-carbide catalyst, followed by introduction of a gaseous mixture consisting of 29.2% by volume of carbon monoxide, 6.2% by volume of hydrogen, 2.2% by volume of n-butyl nitrite and 62.4% by volume of nitrogen at a rate of 39 l. per hour to subject the gaseous mixture to reaction under ambient pressure at a temperature shown below.

The results obtained by gas-chromatographic analyses of the reaction mixtures are shown in the following table.

| Example | Reaction temp. (°C.) | Space time yield of n-butyl formate (g./l.-catalyst · hr) |
|---|---|---|
| 6 | 95 | 146 |
| 7 | 108 | 201 |
| 8 | 120 | 245 |
| 9 | 130 | 249 |
| 10 | 150 | 231 |

In each Example, merely small amounts of di-n-butyl oxalate and n-butanol were observed as by-products.

EXAMPLE 11

In a tubular reactor, there was packed 10 ml. of a 0.5 wt.% palladium-on-alumina catalyst (manufactured by Nippon Engerhard Co., Ltd.), followed by introduction of a gaseous mixture consisting of 28.5% by volume of carbon monoxide, 4.5% by volume of hydrogen, 5.7% by volume of ethyl nitrite and 61.3% by volume of nitrogen at a rate of 40.0 l. per hour to subject the gaseous mixture to reaction at a reaction temperature of 120° C. under ambient pressure. According to a gas-chromatographic analysis of the reaction mixture, it was found that ethyl formate was produced in a space time yield of 235 g./l.-catalyst.hr and small amounts of diethyl oxalate and ethanol were by-produced.

EXAMPLE 12

In a tubular reactor, there was packed 10 ml. of a catalyst in which 0.5% by weight of palladium and 0.1% by weight of platinum were carried on alumina, followed by introduction of a gaseous mixture consisting of 26.7% by volume of carbon monoxide, 2.8% by volume of hydrogen, 6.5% by volume of methyl nitrite and 64.0% by volume of nitrogen at a rate of 42.6 l. per hour to subject the gaseous mixture to reaction at a reaction temperature of 120° C. under ambient pressure. According to a gas-chromatographic analysis of the reaction mixture, it was found that methyl formate was produced in a space time yield of 86 g./l. catalyst.hr and small amounts of dimethyl oxalate and methanol were by-produced.

EXAMPLE 13

In a tubular reactor, there was packed 10 ml. of a 0.5 wt.% palladium chloride-on-alumina catalyst, followed by introduction of a gaseous mixture consisting of 30.0% by volume of carbon monoxide, 3.2% by volume of hydrogen, 1.8% by volume of n-butyl nitrite and 65.0% by volume of nitrogen at a rate of 38 l. per hour to subject the gaseous mixture to reaction at a reaction temperature of 120° C. under ambient pressure. According to a gas-chromatographic analysis of the reaction mixture, it was found that n-butyl formate was produced in a space time yield of 65 g./l.-catalyst.hr and small amounts of di-n-butyl oxalate and n-butanol were by-produced.

EXAMPLE 14

Experiment was run in the same manner as in Example 13 except that the catalyst was replaced by a 0.5 wt.% palladium-nitrate-on-alumina catalyst. As the result, it was found that n-butyl formate was produced in a space time yield of 177 g./l.-catalyst.hr and small amounts of n-butyl oxalate and n-butanol were by-produced.

EXAMPLE 15

In a tubular reactor, there was packed 10 ml. of a pellet catalyst (manufactured by Nippon Engerhard Co., Ltd.), in which 0.5% by weight of rhodium was carried on alumina, followed by introduction of a gaseous mixture consisting of 29.6% by volume of carbon monoxide, 4.7% by volume of hydrogen, 1.8% by volume of n-butyl nitrite and 63.9% by volume of nitrogen at a rate of 38.5 l. per hour to subject the gaseous mixture to reaction at a reaction temperature of 150° C. under ambient pressure. According to a gas-chromatographic analysis of the reaction mixture, it was found that n-butyl formate was produced in a space time yield of 31 g./l.-catalyst.hr.

EXAMPLE 16

Experiment was run in the same manner as in Example 15 except that the catalyst was replaced by a 0.5% ruthenium-on-alumina catalyst. As the result, it was found that n-butyl formate was produced in a space time yield of 18 g./l.-catalyst.hr.

EXAMPLE 17

Experiment was run in the same manner as in Example 11 except that the composition of the gaseous starting materials was replaced by 8.1% by volume of carbon monoxide, 4.1% by volume of hydrogen, 8.3% by volume of methyl nitrite and 79.5% by volume of nitrogen at a rate of 44.4 l. per hour. As the result, it was found that methyl formate was produced in a space time yield of 490 g./l.-catalyst.hr and small amounts of dimethyl oxalate and methanol were by-produced.

EXAMPLE 18

Experiment was run in the same manner as in Example 11 except that the composition of the gaseous starting materials was replaced by 3.6% by volume of carbon monoxide, 2.2% by volume of hydrogen, 3.6% by volume of methyl nitrite and 90.6% by volume of nitrogen at a rate of 39 l. per hour. As the result, it was found that methyl formate was produced in a space time yield of 325 g./l.-catalyst.hr and small amounts of dimethyl oxalate and methanol were by-produced.

EXAMPLE 19

In a tubular reactor made of stainless steel and having an inside diameter of 25 mm and a length of 300 mm was packed with 10 ml. of a catalyst in which 0.5% by weight of palladium was carried on alumina, followed by introduction of a gaseous mixture consisting of 27.0% by volume of carbon monoxide, 2.1% by volume of hydrogen, 7.5% by volume of methyl nitrite and 63.4% by volume of nitrogen at a rate of 40.2 l. per hour under a pressure of 5 Kg./cm$^2$G. to subject the gaseous mixture to reaction at 120° C. According to a gas-chromatographic analysis of the reaction mixture, it was found that methyl formate was formed in a space time yield of 623 g./l.-catalyst.hr and small amounts of dimethyl oxalate and methanol were by-produced.

EXAMPLE 20

In a tubular reactor used in Example 19 was packed 10 ml. of a catalyst in which 0.55% by weight of palladium was carried on alumina (manufactured by Nippon Engerhard Co., Ltd.), followed by introduction of a gaseous mixture consisting of 8.1% by volume of carbon monoxide, 1.8% by volume of hydrogen, 0.2% by volume of cyclohexyl nitrite and 89.9% by volume of nitrogen at a rate of 37.0 l. per hour under an ambient pressure to subject the gaseous mixture to reaction at 120° C.

According to a gas-chromatographic analysis of the reaction mixture, it was found that cyclohexyl formate was formed in a space time yield of 22 g/l.-catalyst.hr and small amounts of cyclohexyl oxalate and cyclohexanol were by-produced.

We claim:

1. A process for the preparation of an ester of formic acid which comprises reacting hydrogen, carbon monoxide and an ester of nitrous acid in a catalytic vapor phase reaction in the presence of a platinum group metal or a salt thereof and at a temperature of not less than 40° C. under a pressure of 0.1 to 100 atmospheres.

2. A process as claimed in claim 1 wherein said ester of nitrous acid is an ester of nitrous acid with an alcohol having 1 to 8 carbon atoms selected from the group consisting of saturated monohydric aliphatic alcohols and alicyclic alcohols.

3. A process as claimed in claim 1 wherein the amounts of hydrogen and carbon monoxide are in the ranges of 0.05 to 10 moles and 0.1 to 100 moles, respectively, relative to one mole of the ester of nitrous acid.

4. A process as claimed in claim 3 wherein the amounts of hydrogen and carbon monoxide are in the ranges of 0.07 to 5 moles and 0.2 to 50 moles, respectively, relative to one mole of the ester of nitrous acid.

5. A process as claimed in claim 1 wherein the reaction is carried out at a temperature of 80° to 200° C. under a pressure of an ambient pressure to 20 atmospheres.

6. A process as claimed in claim 5 wherein the amounts of hydrogen and carbon monoxide are in the ranges of 0.07 to 5 moles and 0.2 to 50 moles, respectively, relative to one mole of the ester of nitrous acid.

7. A process as claimed in claim 5 wherein said ester of nitrous acid is an ester of nitrous acid with an alcohol having 1 to 8 carbon atoms selected from the group consisting of saturated monohydric aliphatic alcohols and alicyclic alcohols.

8. A process as claimed in claim 7 wherein the amounts of hydrogen and carbon monoxide are in the ranges of 0.07 to 5 moles and 0.2 to 50 moles, respectively, relative to one mole of the ester of nitrous acid.

9. A process as claimed in claim 8 wherein said ester of formic acid is methyl formate.

10. A process as claimed in claim 8 wherein said ester of formic acid is n-butyl formate.

11. A process as claimed in claim 8 wherein said ester of formic acid is ethyl formate.

12. A process as claimed in claim 8 wherein said ester of formic acid is cyclohexyl formate.

13. A process for the preparation of an ester of formic acid which comprises reacting hydrogen, carbon monoxide, an alcohol and a nitrogen oxide or a hydrate of the nitrogen oxide in a catalytic vapor phase reaction in the presence of a platinum group metal or a salt thereof and at a temperature of not less than 40° C. under a pressure of 0.1 to 100 atmospheres, and when said nitrogen oxide is nitrogen monoxide, a gas containing molecular oxygen is added to the reactants.

14. A process as claimed in claim 13 wherein said alcohol has 1 to 8 carbon atoms and is selected from the group consisting of saturated monohydric aliphatic alcohols and alicyclic alcohols.

15. A process as claimed in claim 13 wherein said nitrogen oxide is selected from the group consisting of nitrogen monoxide, nitrogen dioxide, dinitrogen trioxide and dinitrogen tetraoxide.

16. A process as claimed in claim 13 wherein said hydrate of the nitrogen oxide is selected from the group consisting of nitric acid and nitrous acid.

17. A process as claimed in claim 13 wherein the reaction is carried out at a temperature of 80° to 200° C. under a pressure of an ambient pressure to 20 atmospheres.

18. A process as claimed in claim 17 wherein said alcohol has 1 to 8 carbon atoms and is selected from the group consisting of saturated monohydric aliphatic alcohols and alicyclic alcohols, and wherein said nitrogen oxide is selected from the group consisting of nitrogen monoxide, nitrogen dioxide, dinitrogen trioxide and dinitrogen tetraoxide.

19. A process as claimed in claim 17 wherein said alcohol has 1 to 8 carbon atoms and is selected from the group consisting of saturated monohydric aliphatic alcohols and alicyclic alcohols, and wherein said hydrate of the nitrogen oxide is selected from the group consisting of nitric acid and nitrous acid.

20. A process as claimed in claim 17 wherein said nitrogen oxide or hydrate of nitrogen oxide is selected from the group consisting of nitrogen monoxide, nitrogen dioxide, dinitrogen trioxide, dinitrogen tetraoxide, nitric acid and nitrous acid and wherein said alcohol is selected from the group consisting of methanol, ethanol, n-butanol, and cyclohexanol.

* * * * *